(12) United States Patent
Morris et al.

(10) Patent No.: US 7,788,731 B2
(45) Date of Patent: Aug. 31, 2010

(54) METHOD AND APPARATUS FOR CUSTOMIZATION

(75) Inventors: Robert Morris, Viola, ID (US); Andrew A. Miller, Moscow, ID (US); Jeffrey L. Hawbaker, Pullman, WA (US)

(73) Assignee: Schweitzer Engineering Laboratories, Inc., Pullman, WA (US)

( * ) Notice: Subject to any disclaimer, the term of this patent is extended or adjusted under 35 U.S.C. 154(b) by 1108 days.

(21) Appl. No.: 11/089,818

(22) Filed: Mar. 25, 2005

(65) Prior Publication Data

US 2006/0218310 A1    Sep. 28, 2006

(51) Int. Cl.
*G06F 1/26* (2006.01)
(52) U.S. Cl. .................. 726/34; 713/300; 713/323; 713/324; 702/62; 702/122; 702/182; 710/13
(58) Field of Classification Search .............. 713/300, 713/323, 324; 726/34; 702/62, 182, 122; 710/13
See application file for complete search history.

(56) References Cited

U.S. PATENT DOCUMENTS

| | | | |
|---|---|---|---|
| 6,279,035 B1 * | 8/2001 | Brown et al. ................. | 709/224 |
| 6,745,254 B2 | 6/2004 | Boggs et al. | |
| 6,813,571 B2 | 11/2004 | Lightbody | |
| 6,885,974 B2 | 4/2005 | Holle | |
| 2002/0049841 A1 * | 4/2002 | Johnson et al. .............. | 709/225 |
| 2002/0108059 A1 * | 8/2002 | Canion et al. ................ | 713/201 |
| 2002/0152305 A1 * | 10/2002 | Jackson et al. .............. | 709/224 |
| 2002/0165677 A1 | 11/2002 | Lightbody | |
| 2004/0003321 A1 | 1/2004 | Glew | |
| 2005/0030693 A1 | 2/2005 | Deak | |
| 2005/0071106 A1 * | 3/2005 | Huber et al. ................. | 702/104 |

FOREIGN PATENT DOCUMENTS

EP     1087294     3/2001

OTHER PUBLICATIONS

Canadian Office Action dated May 22, 2008 to Ridout & Maybee LLP for Application No. 2,600,471; Owner: Schweitzer Engineering Laboratories, Inc.; Title: Method And Apparatus For Customization Of A Protective Device; (Jan. 2006).
Patent Cooperation Treaty (PCT) International Preliminary Report On Patentability; International Appl. No. PCT/US2006/011284; Applicant: Schweitzer Engineering Laboratories, Inc.; Date: Mar. 10, 2009; by Authorized Officer: Nora Lindner.

* cited by examiner

*Primary Examiner*—Kambiz Zand
*Assistant Examiner*—Tongoc Tran
(74) *Attorney, Agent, or Firm*—Eugene M. Cummings, P.C.

(57) ABSTRACT

Provided is an apparatus and method for customization of a protective device. The apparatus and method includes coupling programmer programmable memory to a microprocessor for processing select logic schemes. The programmer programmable memory is adapted to be modifiable by only a programmer of said protective device. Elements associated with some of the logic schemes are implemented into the programmer programmable memory in the form of a compiled settings structure having a plurality of allocation fields.

16 Claims, 5 Drawing Sheets

Compiled Setting Structure

| | |
|---|---|
| 150 — Relay Type | 149 |
| 154 — Max Execution Time | Reference Number — 152 |
| 156 — ID String for VER command | |
| Digital Signature | — 158 |
| 160 — Cold Initialization Code Pointer | Warm Initialization Code Pointer — 162 |
| 164 — Runtime Code Pointer | Settings Validation Code Pointer — 166 |
| 168 — Code Space | |
| | Output Element List — 170 |
| 172 — Settings Structures | |
| Default Settings | — 174 |

METHOD AND APPARATUS FOR CUSTOMIZATION

CROSS-REFERENCE TO RELATED APPLICATIONS

None.

BACKGROUND OF THE INVENTION

The present invention generally relates to power system protection, and more specifically, to a method and apparatus for customization of a protective device.

Electric utility systems or power systems are designed to generate, transmit and distribute electrical energy to loads. In order to accomplish this, power systems generally include a variety of power system elements such as electrical generators, electrical motors, power transformers, power transmission lines, buses and capacitors, to name a few. As a result, power systems must also include protective devices and procedures to protect the power system elements from abnormal conditions such as electrical short circuits, overloads, frequency excursions, voltage fluctuations, and the like.

Protective devices and procedures act to isolate some power system element(s) from the remainder of the power system upon detection of the abnormal condition or a fault in, or related to, the power system element(s). Logically grouped zones of protection, or protection zones utilizing the protective devices and procedures, are established to efficiently manage faults or other abnormal conditions occurring in the power system elements.

Generally, protective devices are also used for protecting, monitoring, controlling, metering and/or automating electric power systems and associated transmission lines. Protective devices may include protective relays, remote terminal units (RTUs), power line communications devices (PLCs), bay controllers, supervisory control and data acquisition (SCADA) systems, general computer systems, meters, and any other comparable devices used for protecting, monitoring, controlling, metering and/or automating electric power systems and their associated transmission lines.

Traditional protective devices generally include various overcurrent, voltage, directional, distance, differential, and frequency protective logic schemes. These logic schemes and the logic elements associated therewith are generally either programmed into user programmable memory or permanently hard coded into fixed memory. Protective devices require flexibility and modification in their processing based on their application in the field. Often, protective device applications are unique in nature. Accordingly, modifications to protective devices used in such applications are similarly unique for a particular user.

In traditional protective devices, some modifications in device processing can be made by the end user (e.g., the customer) by modifying the user programmable memory. For example, the end user may modify the user programmable memory to include custom logic algorithms. Nevertheless, for some complex applications, modification of user programmable memory is insufficient due to inadequate microprocessor capacity or inadequate free volatile memory.

Another traditional approach to modification of protective device processing involves changes in the fixed memory contained permanently in the device. Such fixed memory is alternatively referred to as firmware. Modification of the firmware generally involves changes by the programmer (e.g., the manufacturer) requiring extensive product validation and manufacturing release processes. These validation and release processes are often complicated, costly, and burdensome for both the end user (e.g., customer) and the programmer (e.g., manufacturer).

The cost for modification of firmware in protective devices ranges from a few thousands of dollars, which is rare, to several hundred thousand dollars, which is more common. Therefore, the manufacturer must weigh whether any increase in sales volume and/or revenue expected from each change would warrant the costs for research, development and implementation of each individual firmware modification. Because modifications are often unique in nature, these costs often do not warrant manufacturer changes for unique applications.

In yet another traditional approach to modification of protective device processing, a separate computing platform may be connected to a protective device in order to control device processing. Nevertheless, traditional operating systems for these computing platforms do not have the capacity to execute device processing within a desired time. For example, the computer is unable to execute device processing within the required operation time for the protective device to execute protection, monitoring, control, metering and/or automation of electric power systems and associated transmission lines (e.g., isolating an abnormal condition in the power system as soon as possible so as to not cause damage within the system). The fast processing time required is generally about 4-5 milliseconds.

Thus, it is an object of this invention to provide a method and apparatus which customizes protective devices for all applications. It is further an object of this invention to provide a method and apparatus for customizing a protective device without modifying the device's firmware.

These and other desired benefits of the preferred embodiments, including combinations of features thereof, of the invention will become apparent from the following description. It will be understood, however, that a process or arrangement could still appropriate the claimed invention without accomplishing each and every one of these desired benefits, including those gleaned from the following description. The appended claims, not these desired benefits, define the subject matter of the invention. Any and all benefits are derived from the multiple embodiments of the invention, not necessarily the invention in general.

SUMMARY OF THE INVENTION

In accordance with the invention, an apparatus for customization of a protective device having a microprocessor for processing select logic schemes is provided. The apparatus generally includes programmer programmable memory coupled to the microprocessor. The programmer programmable memory includes elements associated with some of the select logic schemes to be processed by the microprocessor and adapted to be modifiable by only a programmer of said protective device.

In accordance with another embodiment of the invention, an apparatus for customization of a protective device is provided including a microprocessor for processing select logic schemes. Coupled to the microprocessor are a user programmable memory, fixed memory, and programmer programmable memory. The user programmable memory includes elements associated with some of the select logic schemes and is adapted to be modifiable by a user of said protective device. The fixed memory is generally unmodifiable and includes elements associated with some of the select logic schemes. The programmer programmable memory includes elements associated with some of the select logic schemes to be processed by the microprocessor and is adapted to be modifiable by only a programmer of the protective device. The elements associated with the programmer programmable memory are implemented in the form of a compiled settings structure including a plurality of allocation fields.

In accordance with yet another aspect of the invention, provided is a method for customizing a protective device including the steps of coupling programmer programmable memory to a microprocessor; adapting the programmer programmable memory to be modifiable by only a programmer of said protective device; implementing elements associated with some of the select logic schemes in the form of a compiled settings structure having a plurality of allocation fields into the programmer programmable memory; implementing executable code into at least one of the allocation fields; and designating at least one of the allocation fields as a pointer allocation field for specifying a point at which portions of said code is to be executed by the microprocessor.

It should be understood that the present invention includes a number of different aspects or features which may have utility alone and/or in combination with other aspects or features. Accordingly, this summary is not exhaustive identification of each such aspect or feature that is now or may hereafter be claimed, but represents an overview of certain aspects of the present invention to assist in understanding the more detailed description that follows. The scope of the invention is not limited to the specific embodiments described below, but is set forth in the claims now or hereafter filed.

DETAILED DESCRIPTION OF THE INVENTION

The present invention generally relates to a method and apparatus for customization of a protective device. Generally, protective devices are used for protecting, monitoring, controlling, metering and/or automating electric power systems and associated transmission lines. Protective devices may include protective relays, RTUs, PLCs, bay controllers, SCADA systems, general computer systems, meters, and any other comparable devices used for protecting, monitoring, controlling, metering and/or automating electric power systems and their associated transmission lines.

Protective devices generally include various overcurrent, voltage, directional, distance, differential, and frequency protective logic schemes. In accordance with an aspect of this invention, these logic schemes and the logic elements associated therewith are generally either programmed into user programmable memory, programmed into programmer programmable memory, or permanently hard coded into fixed memory. In accordance with the teachings of the present invention, the programmer programmable memory allows for flexibility and modification in protective device processing based on their application in the field.

Although the embodiments described herein are associated with protective relays, it is contemplated that the embodiments may also be associated with any suitable power system control or protective devices such as those described above or below.

Figure 1:
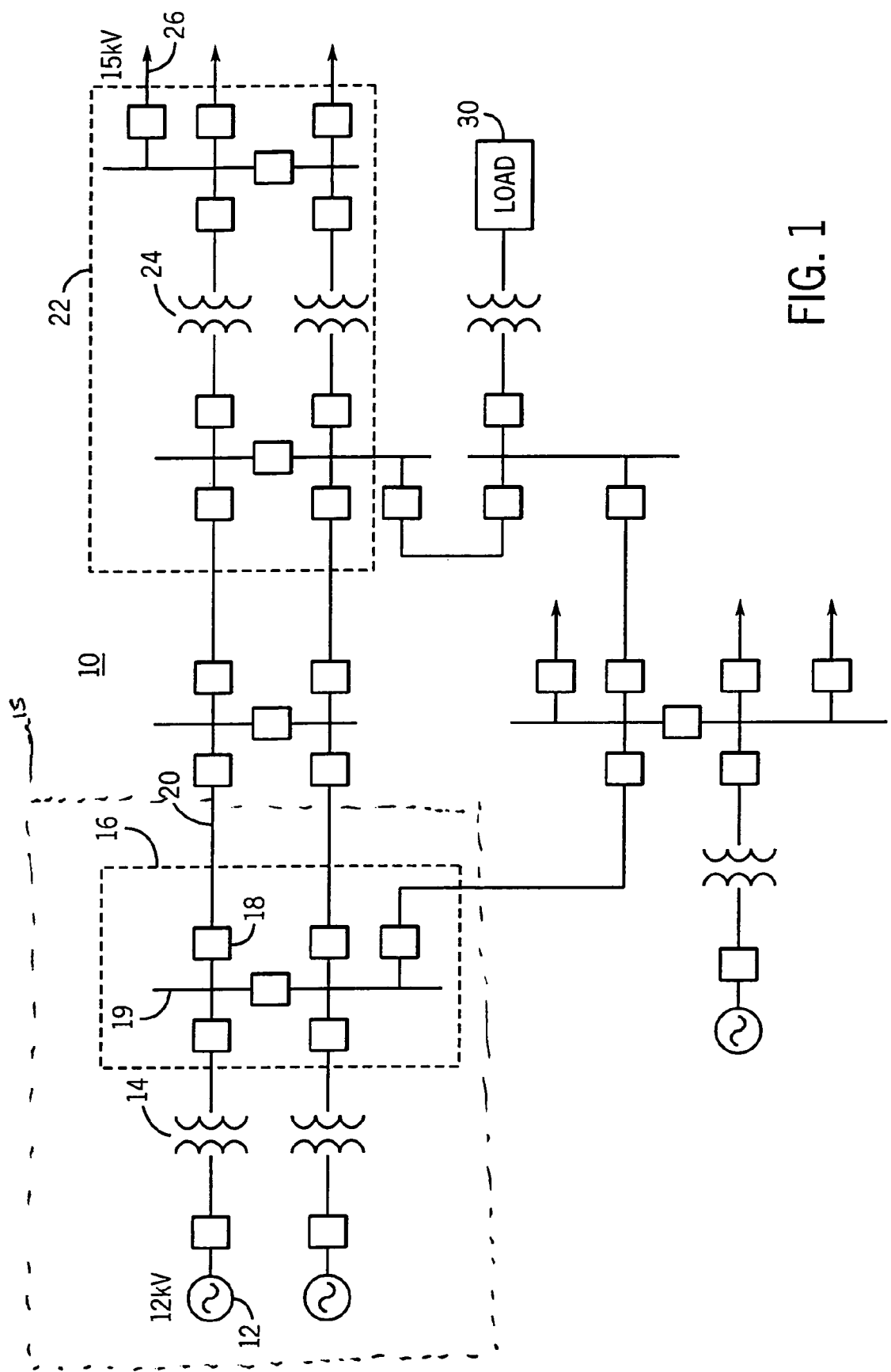
FIG. 1 is a single line schematic diagram of a power system that may be utilized in a typical metropolitan area.

For example, in one application a protective relay may be used to protect and monitor a power system. More specifically, FIG. 1 is a single line schematic diagram of a power system 10 that may be utilized in a typical metropolitan area. As illustrated in FIG. 1, the power system 10 includes, among other things, two generators 12 configured to generate three-phase sinusoidal waveforms, for example, three-phase 12 kV sinusoidal waveforms, two step-up transformers 14 configured to increase the 12 kV sinusoidal waveforms to a higher voltage such as 345 kV and a number of circuit breakers 18. The step-up transformers 14 provide the higher voltage sinusoidal waveforms to a number of long distance transmission lines such as the transmission lines 20.

In one embodiment, a first substation 15 may be defined to include the generators 12, the step-up transformers 14, and the circuit breakers 18, all interconnected via a first bus 19. At the end of the long distance transmission lines 20, a second substation 22 includes step-down transformers 24 to transform the higher voltage sinusoidal waveforms to lower voltage sinusoidal waveforms (e.g., 15 kV) suitable for distribution via a distribution line 26 to various end users and loads.

As previously mentioned, the power system 10 includes protective devices and procedures to protect the power system elements from faults or other abnormal conditions. As will be discussed in further detail below, the protective devices and procedures utilize a variety of protective logic schemes to determine whether a fault or other problem exists in the power system 10. In traditional protective relays, these logic schemes are either programmed into user programmable memory or permanently hard coded into fixed memory. In accordance with the teachings of the present invention, these logic schemes may additionally be programmed into programmer programmable memory.

In one example of utilization of a logic scheme, some types of protective relays utilize a current differential comparison to determine whether a fault exists in the protection zone. Other types of protective relays compare the magnitudes of calculated fundamental phasors, representative of the three-phase sinusoidal waveforms, to determine whether a fault exists in the protection zone. Frequency sensing techniques and harmonic content detection is also incorporated in protective relays to detect fault conditions. Similarly, thermal model schemes are utilized by protective relays to determine whether a thermal problem exists in the protection zone.

Referring again to FIG. 1, a protection zone 16 is established to include a portion of the first substation 15. A protective relay is coupled to the protection zone 16 via a number of current transformers.

Figure 2:
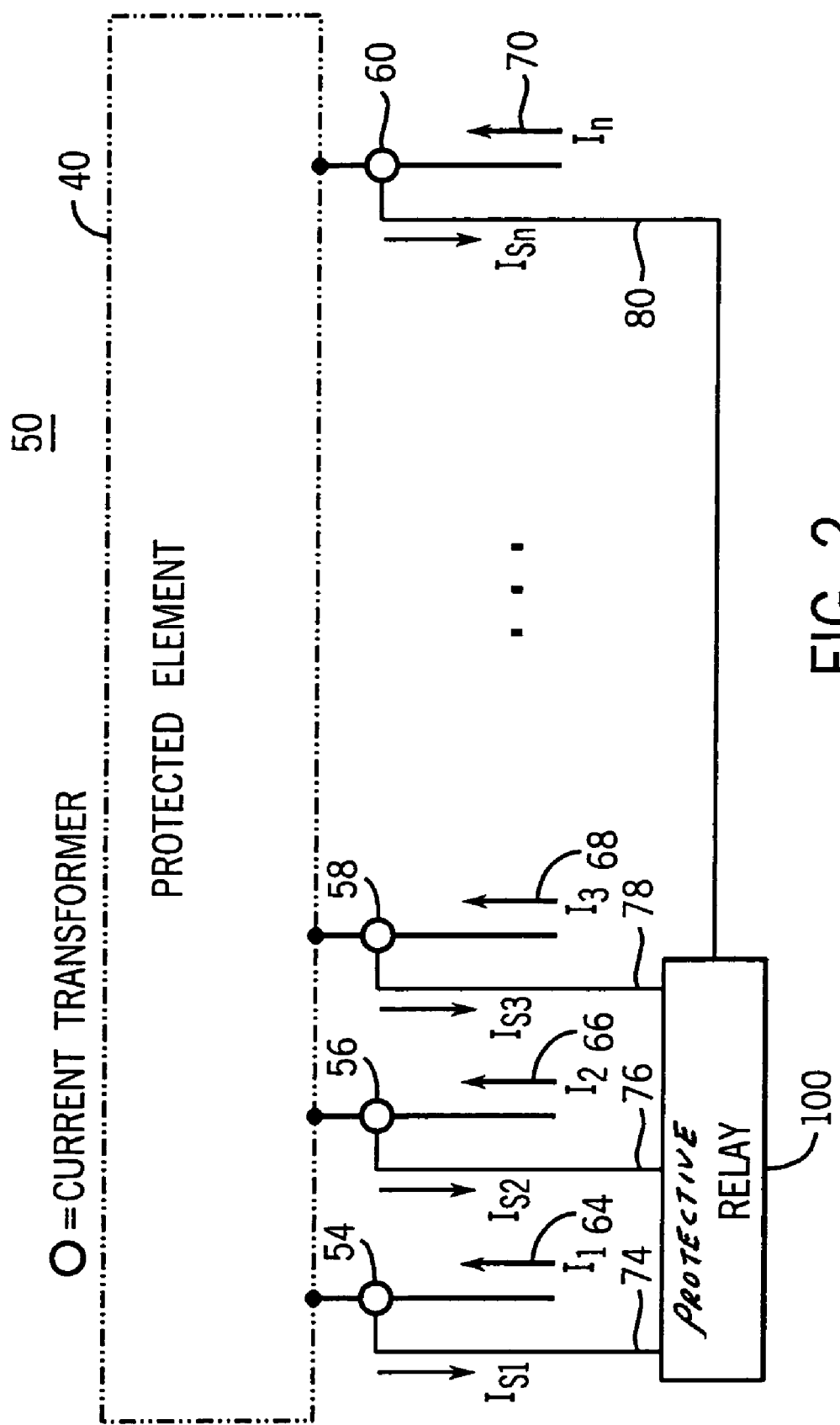
FIG. 2 is a block diagram of a protective relay coupled to the protection zone of the power system of FIG. 1 according to an embodiment of the invention.

FIG. 2 is a block diagram of a protective relay 100 coupled to the protection zone 16 of FIG. 1 according to an embodiment of the invention. Although only one protection zone 16 is included for ease of discussion, the power system 10 may include many overlapping protection zones. Referring to FIGS. 1 and 2, the protection zone 16 is configured to protect a portion of the first substation 15 via operation of the protective relay, coupled to the protection zone via nn current transformers 54, 56, 58 to 60. For ease of discussion, the protective relay is configured as a protective relay 100, adapted to monitor only the A-phase primary currents flowing into the protection zone 16. Thus, two additional protection zones having the same "footprint," may also be configured with two additional respective protective relays to monitor the B-phase and C-phase currents flowing into corresponding protection zones. Alternatively, one protective relay may be configured to monitor more than one protection zone.

Although illustrated using the protective relay 100, it should be noted that other types of protective devices (e.g., a general computer) may be utilized to implement the apparatus and methods disclosed herein. Further, although illustrated as four current transformers, it should be noted that nn current transformers 54, 56, 58 to 60 represent all of the current transformers required to couple the protective relay 100 to the protection zone 16.

As previously mentioned, the protection zone 16 may be defined such that the protective relay 100 utilizes the A-phase secondary current waveforms of the current transformers. Thus, each of the nn current transformers 54, 56, 58 to 60 is configured to step-down the current magnitudes of respective A-phase primary current waveforms 64, 66, 68 to 70 to corresponding secondary current waveforms 74, 76, 78 to 80, having magnitudes suitable for use by the protective relay 100. Further, each of the A-phase primary current waveforms 64, 66, 68 to 70 is equal to respective corresponding secondary current waveforms 74, 76, 78 to 80, multiplied by respective current transformer ratios (turn ratios) of the respective current transformers 54, 56, 58 to 60. For example, $I_1 = n_1 \bar{I}_1$ or $$\bar{I}_1 = \frac{I_1}{n_1}$$

where $n_1$ is the turn ratio of the current transformer 54.

During operation and protection of protected element 40 located in protection zone 16, the protective relay 100 processes the secondary current waveforms 74, 76, 78 to 80 received via respective current transformers 54, 56, 58 to 60. The secondary current waveforms 74, 76, 78 to 80 are filtered, sampled and then digitized for use by a microprocessor (or a field programmable gate array (FPGA)) of the protective relay 100. The microprocessor then calculates a series fundamental phasors, each having a magnitude and phase angle that are representative of each of the A-phase primary current waveforms 64, 66, 68 to 70, and then performs calculations to determine if a short circuit or fault exists in the protection zone 16.

Figure 3:
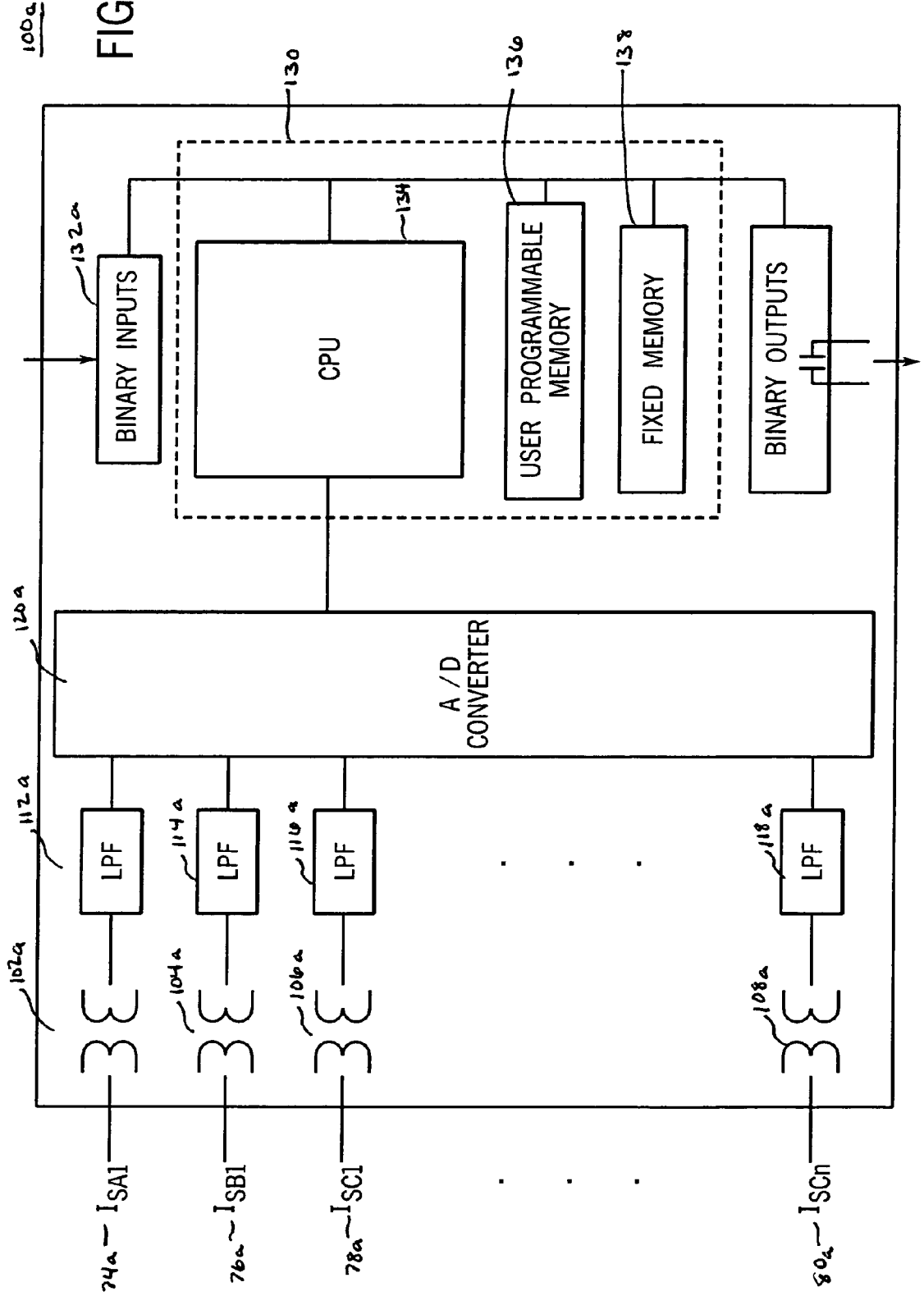
FIG. 3 is a block diagram of an exemplary configuration of a traditional protective relay of FIG. 2.

For example, FIG. 3 is a block diagram of an exemplary configuration of a traditional protective relay 100*a* that may be used in place of protective relay 100 of FIG. 2 where the secondary current waveforms 74*a*, 76*a*, 78*a* to 80*a* are illustrated as $I_{As1}, I_{As2}, I_{As3}$ to $I_{Asmm}$. Although only secondary current waveforms 74*a*, 76*a*, 78*a* to 80*a* are shown in FIG. 3, it should be noted that all secondary current waveforms (i.e., CT signals) of the current transformers 54, 56, 58 to 60 are included.

Referring to FIG. 3, during operation, the secondary current waveforms 74*a*, 76*a*, 78*a* to 80*a* received by the traditional protective relay 100*a* are further transformed into corresponding current waveforms via respective current transformers 102*a*, 104*a*, 106*a*, to 108*a* and resistors (not separately illustrated), and filtered via respective analog low pass filters 112*a*, 114*a*, 116*a* to 118*a*. An analog-to-digital (A/D) converter 120*a* then multiplexes, samples and digitizes the filtered secondary current waveforms to form corresponding digitized current sample streams (e.g., 1011001010001111).

The corresponding digitized current sample streams are received by a microcontroller 130, where they are digitally filtered via, for example, a pair of Cosine filters to eliminate DC and unwanted frequency components. Microcontroller 130 may also be adapted to receive signals via binary inputs 132*a* from other external devices such as protective devices or external computers.

In this traditional relay, the microcontroller 130 includes a microprocessor, or CPU 134, a user programmable memory 136, and fixed memory 138. The traditional relay is adapted to implement overcurrent, voltage, directional, distance, differential, and frequency protective logic schemes. These logic schemes and the logic elements associated therewith are generally either programmed into user programmable memory 136 or permanently hard coded into fixed memory 138. The microprocessor 134 is coupled to the user programmable memory 136 and the fixed memory 138 so that it may access the logic schemes and logic elements associated therewith in order to perform various protective functions.

More specifically, the user programmable memory 136 may include operators, inputs, outputs, algorithms, and logic which may be programmable by the user (e.g., the customer) in order to achieve a particular logic scheme. Modifications in device processing can be made by the end user (e.g., the customer) by modifying the user programmable memory 136. Nevertheless, for some complex applications, modification of user programmable memory 136 is insufficient due to inadequate microprocessor capacity or inadequate free volatile memory. Modification of user programmable memory 136 may further involve complex programming of logic and elements related thereto in order to achieve cooperation with logic already existing within user programmable memory 136 or within fixed memory 138.

Fixed memory 138 may further include operators, inputs, outputs, algorithms, and logic which are preprogrammed by the programmer (e.g., the manufacturer) in order to achieve a particular logic scheme. Unlike the user programmable memory 136, fixed memory 138 (e.g., firmware) is intended to be contained permanently in the device and may not be altered by the end user. Fixed memory 138 is intended to include operators, inputs, outputs, algorithms, and logic for essential device functions. For example, threshold or timer settings are often found in fixed memory 138.

Modification of the fixed memory 138 generally involves a firmware update by the programmer (e.g., the manufacturer). Because of the critical nature of protective device processing, any firmware updating requires extensive product validation and manufacturing release processes. This validation and release processes are often complicated, costly, and burdensome for both the end user (e.g., customer) and the programmer (e.g., manufacturer). The cost for modification of firmware in protective devices ranges from a few thousands of dollars, which is rare, to several hundred thousands of dollars, which is more common. Therefore, the manufacturer must weigh whether any increase in sales volume and/or revenue expected from each change would warrant the costs for research, development and implementation of each individual firmware modification. Because modifications are often unique in nature, these costs often do not warrant manufacturer changes for unique applications.

In yet another traditional approach to modification of protective device processing, a separate computing platform may be connected to a protective device in order to control device processing. In this arrangement, the computing platform would provide input signaling via binary inputs at 132 to augment various microcontroller functions. Nevertheless, traditional operating systems for these computing platforms do not have the capacity to execute device processing within a desired 4-5 milliseconds. The required fast processing time is due to a desired operation time of the protective device to execute protection, monitoring, control, metering and/or automation of electric power systems and associated transmission lines (e.g., isolating an abnormal condition in the power system as soon as possible so as to not cause damage within the system).

Figure 4:
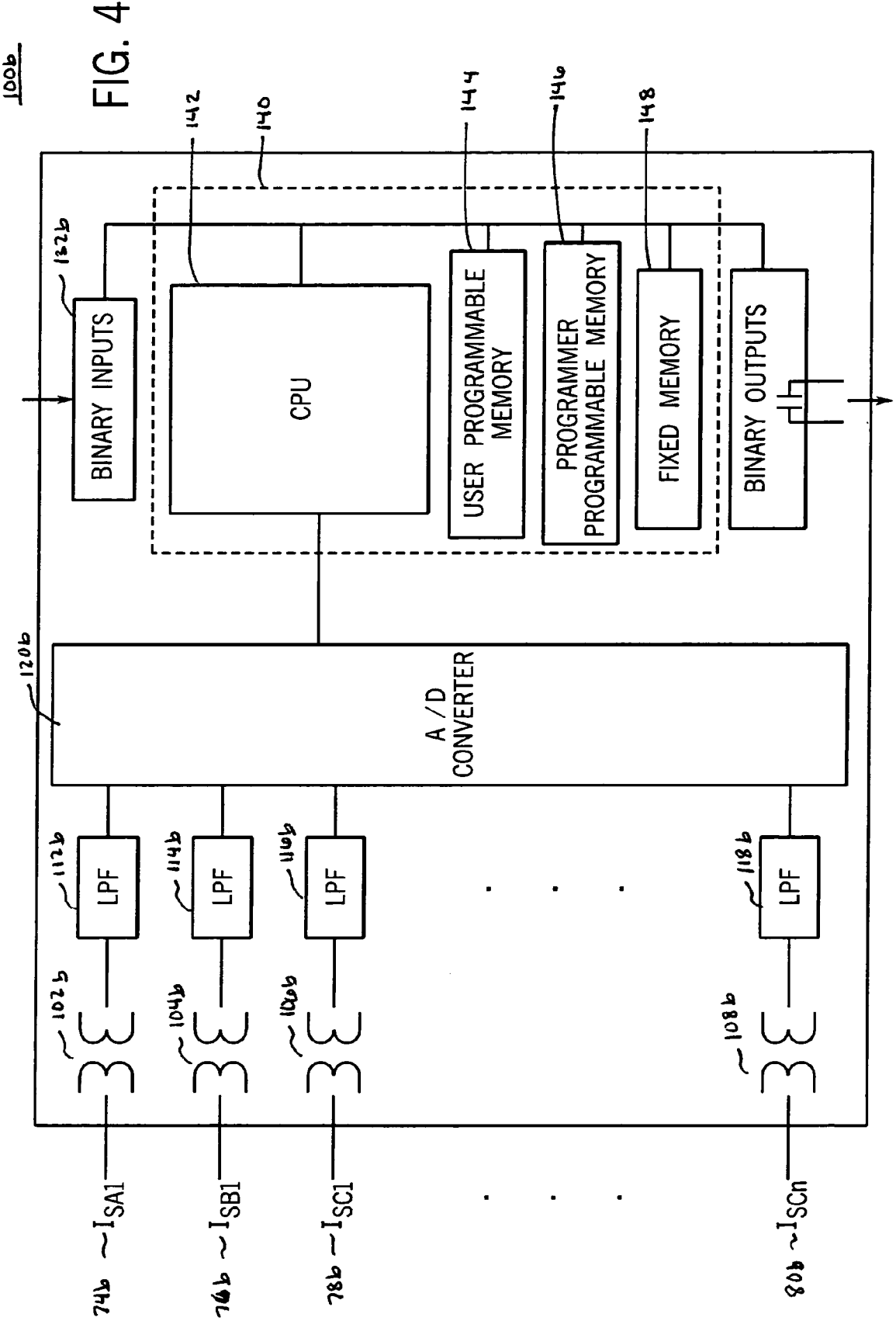
FIG. 4 is a block diagram of an exemplary configuration of an alternative protective relay having programmer programmable memory in accordance with an aspect of the present invention, which may be used in place of the traditional protective relay of FIG. 3.

In order to overcome the shortcomings of modification of protective device processing as described with regard to FIG. 3, microcontroller 140 in accordance with an aspect of the current invention as illustrated in FIG. 4 may replace the microcontroller 130 of FIG. 3.

More specifically, FIG. 4 is a block diagram of an exemplary configuration of a protective relay 100*b* in accordance with an aspect of the current invention. Protective relay 100*b* may generally comprise a similar structure as the protective relay 100*a* of FIG. 1, except for microcontroller 140 of FIG. 4 as compared to microcontroller 130 of FIG. 3. Therefore, the secondary current waveforms 74*b*, 76*b*, 78*b* to 80*b* received by the protective relay 100*b* are transformed into corresponding current waveforms via respective current transformers 102*b*, 104*b*, 106*b*, to 108*b* and resistors (not separately illustrated), and filtered via respective analog low pass filters 112*b*, 114*b*, 116*b* to 118*b*. An analog-to-digital (ND) converter 120*b* then multiplexes, samples and digitizes the filtered secondary current waveforms to form corresponding digitized current sample streams (e.g., 1011001010001111).

The corresponding digitized current sample streams are received by a microcontroller 140, where they are digitally filtered via, for example, a pair of Cosine filters to eliminate DC and unwanted frequency components. Microcontroller 140 may also be adapted to receive binary inputs 132*b* from other external devices such as protective devices or external computers. Binary inputs 132*b* may include, among other things, data streams as those described in U.S. Pat. No. 5,793,750 for "System for Communicating Output Function Status Indications Between Two or More Power System Protective Relays" and U.S. patent application Ser. No. 09/900,098 for "Relay-to-Relay Direct Communication System in an Electric Power System," both of which are incorporated herein in their entirety and for all purposes.

In this relay in accordance with an aspect of the present invention, the microcontroller 140 includes a microprocessor, or CPU 142, a user programmable memory 144, programmer programmable memory 146, and fixed memory 148. The relay is adapted to implement overcurrent, voltage, directional, distance, differential, and frequency protective logic schemes. These logic schemes and the logic elements associated therewith are generally either programmed into user programmable memory 144, programmed into programmer programmable memory 146, or permanently hard coded into fixed memory 148. The microprocessor 142 is coupled to the user programmable memory 144, the programmer programmable memory 146, and the fixed memory 138 so that it may access the logic schemes and logic elements associated therewith in order to perform various protective functions.

More specifically, the user programmable memory 144 may include operators, inputs, outputs, algorithms, and logic which may be programmable by the user (e.g., the customer) in order to achieve a particular logic scheme. Modifications in device processing can be made by the end user (e.g., the customer) by modifying the user programmable memory 144. Such modification is intended for routine applications, which do not hinder microprocessor capacity nor require a large amount of free volatile memory.

Fixed memory 148 may include operators, inputs, outputs, algorithms, and logic which are preprogrammed by the programmer (e.g., the manufacturer) in order to achieve a particular logic scheme. Unlike the user programmable memory 144, fixed memory 148 (e.g., firmware) is intended to be contained permanently in the device and may not be altered by the end user. Fixed memory 148 is intended to include operators, inputs, outputs, algorithms, and logic for essential device functions. For example, threshold or timer settings may be stored in fixed memory 148.

Programmer programmable memory 146 is a nonvolatile memory location which may include operators, inputs, outputs, algorithms, and logic programmable by the programmer (e.g., the manufacturer) in order to achieve a particular logic scheme. For example, such logic elements for a particular logic scheme are saved in the form of compiled settings within programmer programmable memory 146. In one embodiment, the compiled settings may be downloaded in compiled settings file format, decoded, and saved to the programmer programmable memory 146 in executable form. In turn, the microprocessor 140 retrieves the compressed compiled settings code and data, and temporarily saves the code and data associated therewith into a volatile memory location. The processing of the code and data from programmer programmable memory 146 is handled in an analogous fashion as the data from user programmable memory 144, once the data from user programmable memory has been compiled.

Figure 5:
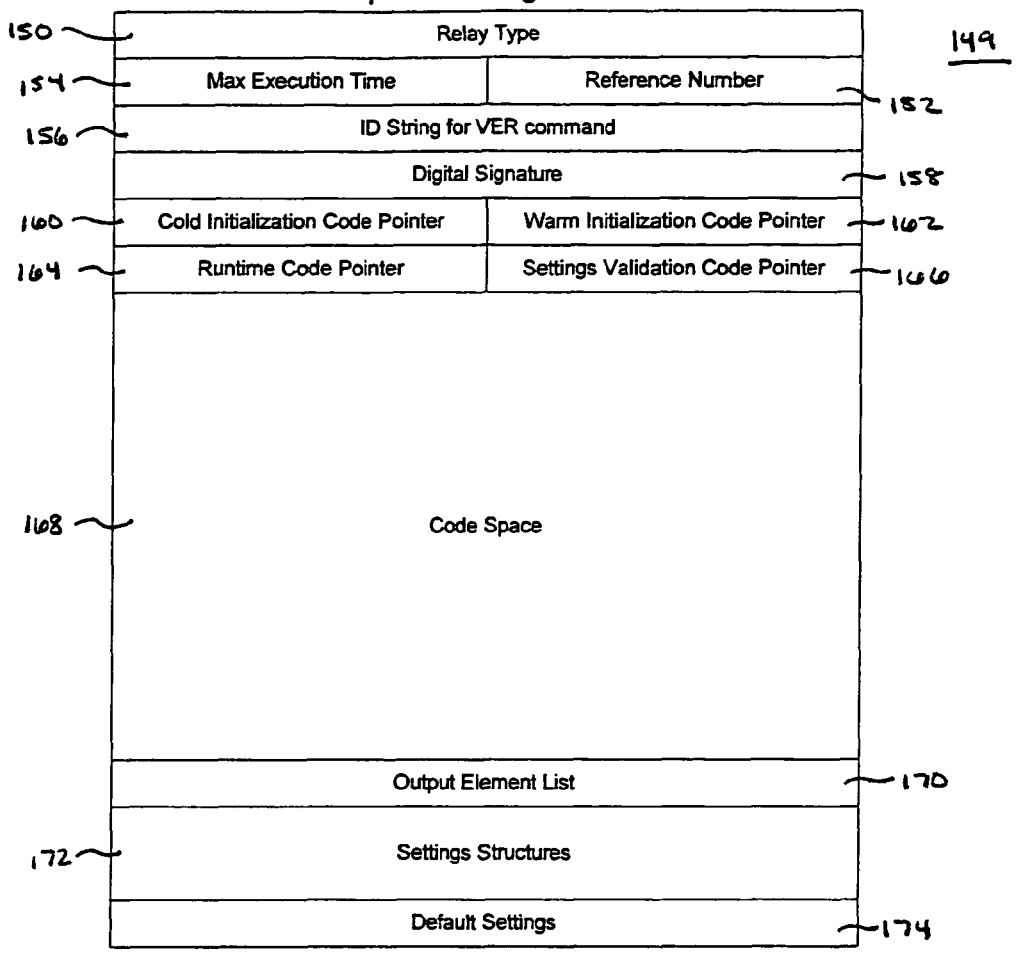
FIG. 5 illustrates a detailed structural diagram of a compiled settings code and data structure implemented in the programmer programmable memory of FIG. 4 in accordance with an aspect of the present invention.

FIG. 5 illustrates a detailed structural diagram of compiled settings code and data structure implemented in the programmer programmable memory 146 of FIG. 4 in accordance with an aspect of the present invention. In this embodiment, the programmable memory includes a compiled settings structure for organizing logic elements (e.g., operators, inputs, outputs, algorithms, logic and the like) associated with a particular logic scheme into select allocation fields. For example, the compiled settings structure may include an allocation field for specifying "Relay Type" 150. This allocation field specifies the type of relay associated with the compiled settings, thereby allowing the microprocessor to check this allocation field to ensure the particular compiled settings is appropriate. For example, the microprocessor compares this "relay type" allocation field with an associated element in the fixed memory, thereby ensuring that the particular compiled settings is appropriate. Without deviating from the teachings of the present invention, this allocation field may alternatively specify any other protective device.

A "Reference Number" 152 allocation field is provided for specifying the specific version of relay, otherwise referred hereinafter as "relay word", associated with the compiled settings. The microprocessor further checks this allocation field to ensure that the compiled settings will not cause an internal conflict or problem related thereto. For example, the microprocessor compares this "reference number" allocation field with an associated element in the fixed memory, thereby ensuring that the particular compiled settings is appropriate and will not cause an internal conflict related thereto. Any relay word conflicts may thereupon be signaled at settings save time and at settings change time. Without deviating from the teachings of the present invention, this allocation field may alternatively specify any other protective device.

A "Max Execution Time" 154 allocation field is provided for specifying how long associated code in the compiled settings will take to execute, thereby enabling the microcontroller to calculate the total execution time for all compiled settings downloaded in the programmer programmable memory. This enables the relay to ensure that the execution time does not exceed a select threshold stored in the fixed memory. Generally, this threshold is programmed and established by relay designers to ensure all algorithms complete in the allocated time. This time may further be used to calculate the processing rate needed to support the compiled settings via an algorithm stored in the fixed memory.

An "ID String for VER command" 156, or alternatively a "SHO command," allocation field is provided for specifying a listing and description of compiled settings stored in the in programmer memory 146, thereby allowing the user to determine what algorithms are loaded into programmer memory 146. A "Digital Signature" 158 allocation field specifies the origin of the compiled settings. With this allocation field, the user may compare the digital signature value to a value published by the programmer to ensure that the compiled settings originated from that programmer. The microprocessor further calculates a digital signature for the compiled settings, and compares it to a digital signature stored in the fixed memory. If the digital signature and stored digital signature do not match, the microcontroller provides a binary output signal to signal such. This binary output signal may ultimately be used to signal an error at settings change or download time.

The compiled settings structure may further include pointer allocation fields for specifying a point at which portions of executable code is to be executed by the microprocessor. A "Cold Initialization Code Pointer" 160 allocation field is provided for specifying a pointer to the associated code that requires execution at power-up or other cold initiation times. A "Warm Initialization Code Pointer" 162 allocation field specifies a pointer to the associated code that requires execution at a settings change or other warm initiation times (e.g., for performing actions such as initialization of binary outputs). A "Run Time Code Pointer" 164 allocation field is provided for specifying a pointer to associated code that is executed every processing interval. This associated code is analogous to certain compiled code in user programmable memory. A "Settings Validation Code Pointer" 166 allocation field specifies a pointer to associated code that verifies the validity of any new settings used by the compiled settings to allow user entered parameters.

A "Code Space" 168 field allocation contains all of associated code mentioned in the previous paragraph. An "Output Element List" 170 field allocation is provided for specifying, preferably in listing format, the logic elements, as designated by the "Reference Number" 152 allocation field, that are being modified by the code contained in 168. In one embodiment, this list can be used to customize a user interface associated therewith.

A "Settings Structures" 172 allocation field contains any compiled settings which require comparison with thresholds. The microprocessor uses settings routines stored in the fixed memory coupled with this allocation field to prompt for, check the limits of, and store new settings required by the code contained in 168. A "Default Settings" 174 allocation field is further provided comprising default values for the new settings defined in the "Settings Structures" 172.

Without deviating from the teachings of the current invention, a plurality of compiled settings structures as outlined above may be implemented in programmer programmable memory. Moreover, each such compiled setting structure may include any or all of the allocation fields described above. A number of other allocation fields comprising additional logic elements not discussed herein may also be included. For example, the programmer programmable memory may include a compiled settings structure having any of the allocation fields as discussed above coupled with yet another compiled settings structure having a similar or even different allocation fields.

Figure 6:
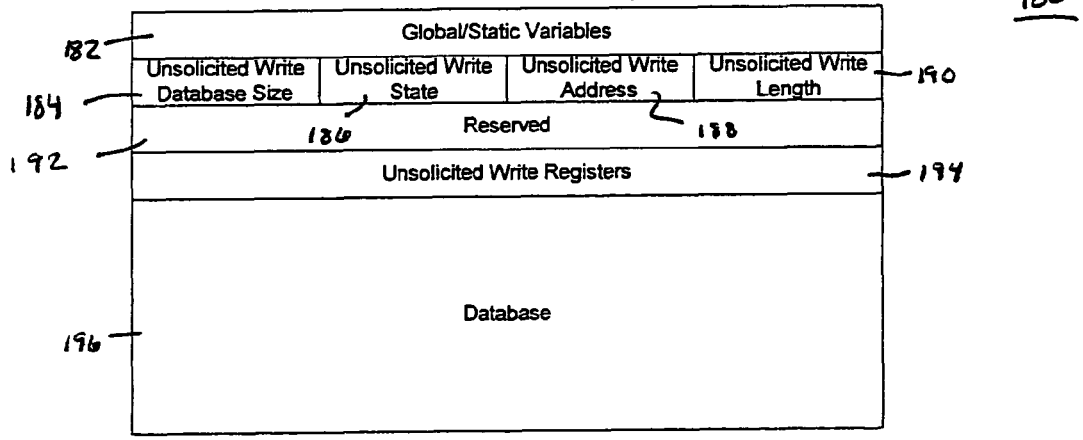
FIG. 6 illustrates a detailed structural diagram of volatile memory associated with the programmer programmable memory of FIG. 4.

FIG. 6 illustrates a detailed structural diagram of volatile memory or random access memory (RAM) 180 associated with the programmer programmable memory in accordance with an aspect of the present invention. In this embodiment, the volatile memory includes a plurality of allocation fields. For example, the "Global/Static Variables" 182 allocation field provides a temporary copy of user entered parameters and variables required by the programmer programmable memory 146. The "Unsolicited Write Database Size" 184 allocation field contains the size of the "Database" field that is used by the programmer programmable memory 146.

The "Unsolicited Write State" 186 allocation field is used for arbitration of the "Unsolicited Write Address" 188 allocation field, the "Unsolicited Write Length" 190 allocation field, and the "Unsolicited Write Register" 194 allocation field between the fixed memory code 148 and the programmer programmable memory code. The fixed memory code updates the "Unsolicited Write Address" 188 allocation field, the "Unsolicited Write Length" 190 allocation field, and the "Unsolicited Write Register" 194 allocation field based on data received from the user through the use of unsolicited fast messages. The compiled settings code uses these fields to update the "Database" 196 allocation field for its own use.

In accordance with the aspects described with regard to the present invention above, modifications in device processing can be made by the programmer (e.g., the manufacturer) by providing programmer programmable memory in a protective device and allowing for modification of such. Data including operators, inputs, outputs, algorithms, and logic for particular logic schemes may be saved in the programmer programmable memory. It is further intended that the end user would not be able to modify programmer programmable memory. Moreover, in order to ensure proper entry of a compiled settings structure, the settings file is required to have a proper format.

For example, in one embodiment, the programmer (e.g. manufacturer) may build an application and data to conform to a compiled settings structure as described in FIG. 5. Resultant data is placed into a compiled settings file format, which is downloadable by the user into the programmer programmable memory of the protective device. Through fixed memory, the protective relay validates and saves the data into the programmer programmable memory. More specifically, all data and code contained in the compiled settings file is required to fall within a select address range. Otherwise, the compiled settings file is rejected. Also, before the data is saved to the programmer programmable memory, the Relay Type, and Reference Number are checked against elements stored in fixed memory, the Digital Signature is verified, the Max Execution Time is combined with the comparable values for the existing settings in the protective device and compared to a threshold in fixed memory, and the pointers are all verified to point to valid locations within the Code Space.

By programming operators, inputs, outputs, algorithms, and logic into programmer programmable memory, the user programmable memory would not require modification. Accordingly, microprocessor would not unnecessarily consume computing resources and free volatile memory. In another benefit of programmer programmable memory, fixed memory (e.g., firmware) would not require modification. Therefore, modification would not require extensive product validation and manufacturing release processes. For example, research and design validation, manufacturing process verification, user literature modification, marketing collateral modification, and executive management oversight are not required. In yet another benefit for the programmer programmable memory, a separate computing platform is not required to control or manipulate device processing.

While this invention has been described with reference to certain illustrative aspects, it will be understood that this description shall not be construed in a limiting sense. Rather, various changes and modifications can be made to the illustrative embodiments without departing from the true spirit, central characteristics and scope of the invention, including those combinations of features that are individually disclosed or claimed herein. Furthermore, it will be appreciated that any such changes and modifications will be recognized by those skilled in the art as an equivalent to one or more elements of the following claims, and shall be covered by such claims to the fullest extent permitted by law.

What is claimed is:

1. An apparatus for customization of a protective device, said apparatus comprising:
   a microprocessor for processing logic schemes associated with protection of power system elements, said microprocessor configured to have select operating intervals;
   fixed memory coupled to the microprocessor and defining some of the logic schemes for processing by said microprocessor; and
   programmer programmable memory coupled directly to said microprocessor and modifiable by only a programmer of the protective device, said programmer programmable memory including code space having a compiled settings structure including a plurality of allocation fields, wherein one of the allocation field includes portions of executable code and at least some of the other allocation fields are pointer allocation fields, each being associated with one of the microprocessor operating intervals, wherein each portion of executable code is associated with a select logic scheme to be processed by said microprocessor and wherein each portion of executable code is further associated with one of the pointer allocation fields for specifying the operating interval at which the portion of executable code is to be executed by the microprocessor such that the fixed memory does not require modification during customization of the apparatus.

2. The apparatus for customization of a protective device of claim 1, further including user programmable memory coupled to said microprocessor, said user programmable memory including portions of executable code associated with some of the select logic schemes and modifiable by a user of said protective device.

3. The apparatus for customization of a protective device of claim 1, wherein the protective device is a protective relay.

4. The apparatus for customization of a protective device of claim 1, wherein the portions of executable code are selected from a group consisting of operators, inputs, outputs, algorithms, code, and logic.

5. The apparatus for customization of a protective device of claim 1, wherein the logic scheme processed by said microprocessor is selected from a group consisting of overcurrent, voltage, directional, distance, differential, and frequency protective logic schemes.

6. The apparatus for customization of a protective device of claim 1, wherein one of the other allocation fields is a protective device allocation field for specifying a particular type of protective device associated with the compiled settings.

7. The apparatus for customization of a protective device of claim 1, wherein one of the other allocation fields is a reference allocation field for specifying a particular version of protective device associated with the compiled settings.

8. The apparatus for customization of a protective device of claim 1, wherein one of the other allocation fields is a digital signature allocation field for specifying the programmer of said programmer programmable memory.

9. The apparatus for customization of a protective device of claim 1, wherein one of the other allocation fields is an execution time allocation field for specifying the duration for executing each portion of executable code.

10. The apparatus for customization of a protective device of claim 1, wherein one of the portions of executable code includes code requiring execution during cold initialization operating interval of said protective device, and wherein one of the pointer allocation fields specifies that the portion of executable code is to be executed during the cold initialization operating interval of the protective device.

11. The apparatus for customization of a protective device of claim 1, wherein one of the portions of executable code includes code requiring execution during warm initialization operating interval of said protective device, and wherein one of the pointer allocation fields specifies that the portion of executable code is to be executed during the warm initialization operating interval of the protective device.

12. The apparatus for customization of a protective device of claim 1, wherein one of the pointer allocation fields is a run time code pointer allocation field for specifying the portion of executable code requiring execution during the select processing interval.

13. The apparatus for customization of a protective device of claim 1, wherein one of the portions of executable code includes code requiring verification, and wherein one of the pointer allocation fields is a settings validation code pointer allocation field for specifying the portion of executable code requiring validation.

14. The apparatus for customization of a protective device of claim 1, wherein one of the allocation fields is a settings structure allocation field including any elements requiring comparisons to associated thresholds.

15. The apparatus for customization of a protective device of claim 1, wherein one of the allocation fields is a default settings allocation field including default values for associated elements.

16. The apparatus for customization of a protective device of claim 5, further comprising volatile memory coupled to both the microprocessor and the programmer programmable memory.

* * * * *